(12) United States Patent
Rochat

(10) Patent No.: US 8,070,667 B2
(45) Date of Patent: Dec. 6, 2011

(54) DISPOSABLE ASSEMBLY FOR SEPARATING BLOOD OR SCRUBBING A BLOOD COMPONENT

(76) Inventor: Jean-Denis Rochat, Genolier (CH)

(*) Notice: Subject to any disclaimer, the term of this patent is extended or adjusted under 35 U.S.C. 154(b) by 357 days.

(21) Appl. No.: 12/444,788

(22) PCT Filed: Oct. 4, 2007

(86) PCT No.: PCT/CH2007/000491
§ 371 (c)(1),
(2), (4) Date: Apr. 8, 2009

(87) PCT Pub. No.: WO2008/043190
PCT Pub. Date: Apr. 17, 2008

(65) Prior Publication Data
US 2010/0048373 A1  Feb. 25, 2010

(30) Foreign Application Priority Data
Oct. 10, 2006 (EP) .................................. 06405432

(51) Int. Cl.
*B04B 7/02* (2006.01)
(52) U.S. Cl. .......................................... 494/41; 494/60
(58) Field of Classification Search .................. 494/12, 494/23–30, 36, 38, 56, 41, 43, 67, 83–85, 494/60; 210/782
See application file for complete search history.

(56) References Cited

U.S. PATENT DOCUMENTS

| | | | |
|---|---|---|---|
| 3,073,517 A * | 1/1963 | Pickels et al. | 494/67 |
| 5,100,372 A * | 3/1992 | Headley | 494/41 |
| 5,141,486 A * | 8/1992 | Antwiler | 494/37 |
| 2002/0032112 A1 * | 3/2002 | Pages | 494/36 |
| 2004/0245189 A1 | 12/2004 | Robinson et al. | |
| 2006/0199720 A1 | 9/2006 | Juan | |
| 2008/0128367 A1 * | 6/2008 | Rochat | 210/782 |
| 2008/0132397 A1 * | 6/2008 | Rochat | 494/45 |
| 2008/0153686 A1 * | 6/2008 | Rochat | 494/45 |
| 2008/0264841 A1 * | 10/2008 | Rochat | 210/120 |
| 2009/0050579 A1 * | 2/2009 | Rochat et al. | 210/772 |
| 2009/0065424 A1 * | 3/2009 | Rochat | 210/380.3 |
| 2010/0048373 A1 * | 2/2010 | Rochat | 494/41 |

FOREIGN PATENT DOCUMENTS

| | | | |
|---|---|---|---|
| EP | 1683578 A1 | | 7/2006 |
| JP | 2005081087 A | * | 3/2005 |
| WO | 84/02473 A1 | | 7/1984 |

OTHER PUBLICATIONS

International Search Report of PCT/CH2007/000491, date of mailing Jan. 24, 2008. Written Opinion of the International Searching Authority (Form PCT/ISA1237) of International Application No. PCT/CH2007/000491.

* cited by examiner

*Primary Examiner* — Charles E Cooley
(74) *Attorney, Agent, or Firm* — Westerman, Hattori, Daniels & Adrian, LLP

(57) ABSTRACT

The invention relates to a centrifugation enclosure (1) made of rigid plastic that comprises a member (1*b*) adapted to engage with the driving organ of a centrifugation machine (M) and a communication member (5) between the enclosure (1) and the outside, made of rigid plastic and comprising un first duct (5*a*) extending therethrough for supplying said enclosure (1) as well as two ducts (5*b*, 5*c*) extending therethrough for discharging the separated components. A holder (3) made of rigid plastic and having a network of channels (4*a*, 4*b*, 4*c*) formed therein connects the ducts (5*a*, 5*b*, 5*c*), respectively, to supply (P1) and reception (P2, P3) tanks, with side sealing members (6) of said channel network (4*a*, 4*b*, 4*c*). The ends of the ducts (5*a*, 5*b*, 5*c*) are adjacent to the respective ends of the channels (4*a*, 4*b*, 4*c*), and the ends of the ducts (5*a*, 5*b*, 5*c*) have surfaces mating with the end surfaces of the respective channels (4*a*, 4*b*, 4*c*), said mating surfaces being connected to one another.

20 Claims, 9 Drawing Sheets

DISPOSABLE ASSEMBLY FOR SEPARATING BLOOD OR SCRUBBING A BLOOD COMPONENT

BACKGROUND ART

The present invention relates to a disposable assembly for separating blood or the washing of a blood component by centrifugation, comprising a circular centrifuge chamber made of a rigid plastic, comprising, at an end lying on its axis of rotation, an element shaped in order to mesh with a drive member of a centrifuge machine and, at an opposite end, a member for interaction of said chamber with the outside made of a rigid plastic, connected to said centrifuge chamber by a rotary joint and passed through by a tube to supply this chamber and by at least one outlet tube for draining one of the separate constituents, a support made of a rigid plastic in which a network of channels is formed in order to connect said tubes respectively to a supply reservoir for the blood to be separated and to respective reception reservoirs for the separated constituents, elements for laterally closing this network of channels in a sealed manner and means for circulating the fluids through this network of channels from the supply reservoir to the reception reservoirs.

The single-use centrifugation assemblies used to separate blood components from whole blood comprise two main parts: a movable part corresponding to the centrifuge chamber and a fixed part comprising storage pouches for blood components, flexible tubing, and all the parts intended to be connected to the machine controlling the process of separating blood components, such as the interfaces with the pressure sensors, the pumps, the air detectors, the clamps in particular. The centrifuge chamber may be made of a rigid plastic.

Generally speaking, the term "rigid" used in the description and the claims to qualify the plastic materials used relates to materials that are neither flexible, nor soft, nor pliant, i.e. to plastics capable of preserving their initial shape in the conditions of use for which they have been designed.

In the centrifuge assemblies mentioned above, the connection between the movable part and the fixed part is always made using flexible tubing which considerably inhibits the mounting of the centrifuge assembly on the machine, appreciably increasing the working time of the operator and the risk of defective mounting.

It has already been proposed to integrate various elements of a blood separation device on a rigid support, without all the same eliminating the flexible tubes between the centrifuge chamber and the fixed part of the assembly.

WO 8,402,473 shows a molded structure for a plasma fractionation machine comprising fluid flow channels and a membrane filter for separating the plasma from the whole blood. It is not therefore concerned with separation by centrifugation.

US 2004/0245189 relates to a single-use separation assembly comprising a cassette comprising a frame made of injection-molded plastic that supports tubing ultrasonically welded to the frame and a continuous flow centrifuge chamber. The centrifuge chamber is connected in a removable manner to the frame of the cassette in order to be able to be inserted easily into a rotor of the centrifuge during installation of the cassette, so that the centrifuge chamber is uncoupled from the frame of the cassette when the door of the centrifuge apparatus is closed. The connection between the fixed connecting tubes for connecting the centrifuge chamber to the outside and the tubes respectively joined to the centrifuge chamber is produced using a rotating cylindrical part having, on its outer face, a series of annular channels, a fixed part having a face adjacent to the external face of the rotating cylindrical part is passed through by tubes opening onto this adjacent face, at respective radial distances from the axis of the rotating cylindrical part chosen to bring each tube to interact with an annular channel of the rotating part. The seal between the rotating cylindrical part and the fixed part is ensured by an elastic pressure of the adjacent faces of these two parts. Given the rotation speed of the centrifuge chamber, such a solution poses serious heating problems which is capable of damaging the processed blood passing into the annular channels formed on the rotating cylindrical part, and in the tubes of the fixed part pressed elastically against the rotating part, rotating at several thousand rotations/minute to guarantee the seal in the fluid flow.

SUMMARY OF THE INVENTION

The aim of the present invention is to solve these problems at least partly.

To this end, the subject of the present invention is a disposable assembly for separating blood by centrifugation of the type mentioned above, characterized in that the ends of the tubes passing through the member causing the chamber to interact with the outside, concentric with the axis of rotation, are adjacent to the respective ends of the channels, in that the ends of the tubes have surfaces complementary to the surfaces of the ends of the respective channels, and in that these complementary surfaces are fixed to each other by joints in a sealed manner so that said support and said member for causing said chamber to interact with the outside form a rigid assembly.

BRIEF DESCRIPTION OF THE DRAWINGS

The appended drawings illustrate, schematically and by way of example, two embodiments of the disposable assembly for blood separation which is the subject of the present invention.

DETAILED DESCRIPTION OF PARTICULAR EMBODIMENTS

Figure 2:
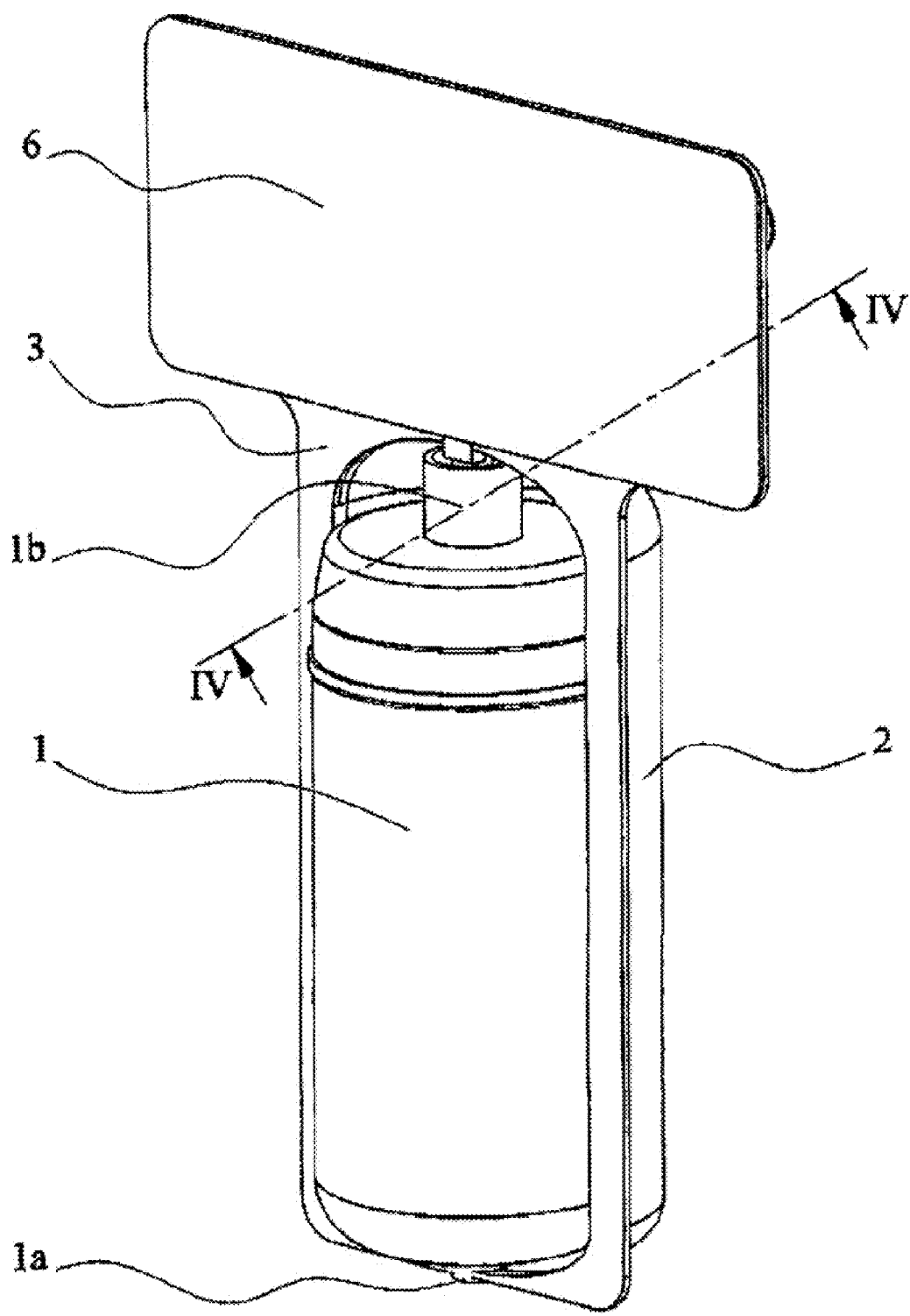
FIG. 2 is perspective view of the disposable assembly alone.
Figure 3:
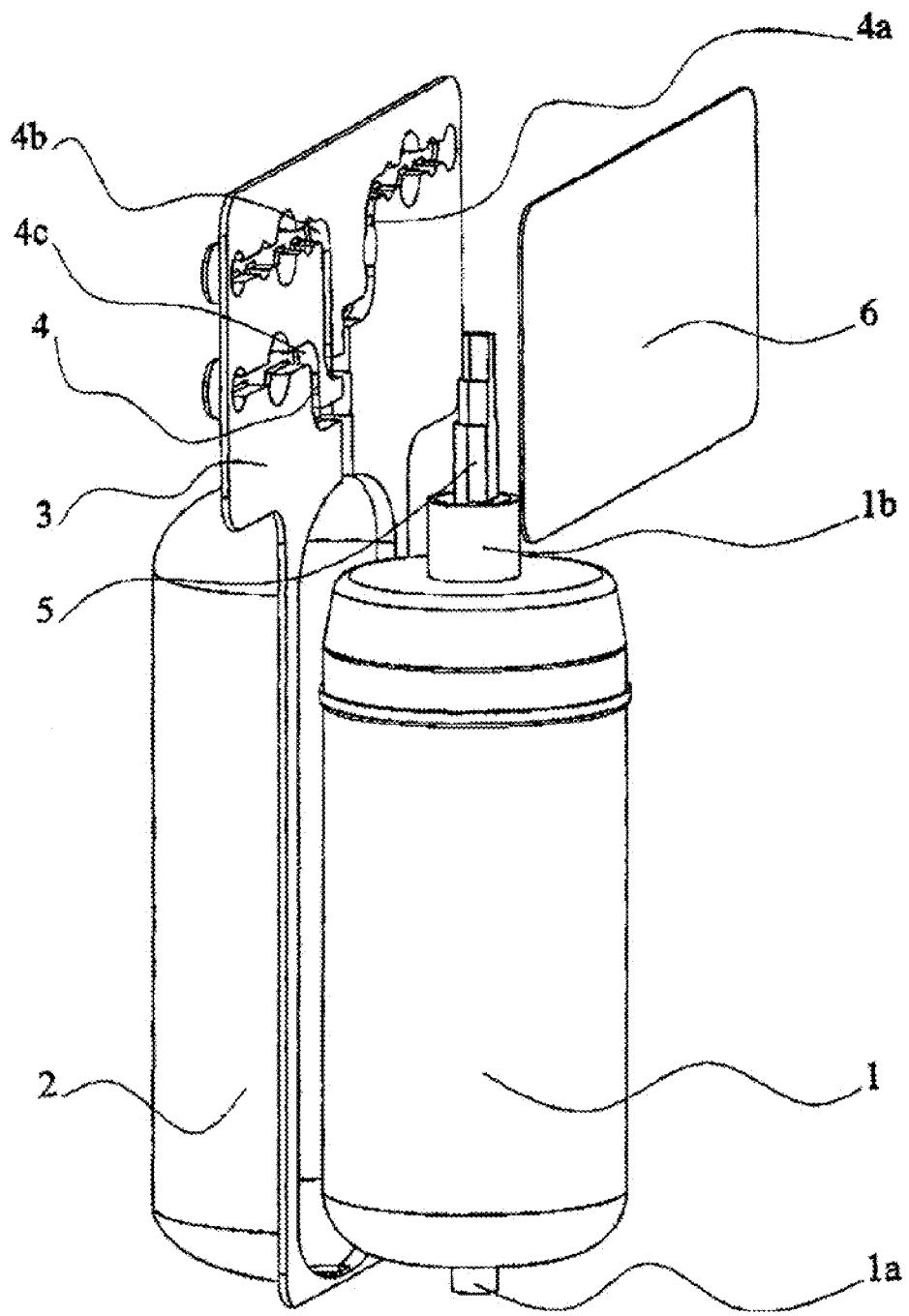
FIG. 3 is an exploded perspective view of the disposable assembly of FIG. 2.

The disposable assembly for separating blood or the washing of a blood component by centrifugation is illustrated by FIG. 2. It comprises a centrifuge chamber 1 having the form of an elongate cylinder partly housed in a semicylindrical case 2 joined to a support 3 in which a network of channels 4 is formed. This support 3 is preferably a generally planar support, only the network of channels 4 forming a relief relative to this plane. All these elements are made of a rigid plastic, preferably by injection. The channels 4 are open laterally onto a face of the planar support 3, a flexible membrane 6 being fixed by welding or by bonding to the face of the planar support onto which the channels 4 open, so that these channels 4 then form tubes that are open only at their two ends. This membrane 6 is made of a flexible plastic such as silicone, PUR, PVC plus plasticizer, EPDM.

The centrifuge chamber 1 comprises an element coupling the coaxial to its axis of rotation and projecting at its lower end, through an opening formed in the base of the semicylindrical case 2. This coupling element 1a has inside a housing of noncircular shape to mesh with a drive member (not shown) of complementary shape of the centrifuge machine M, illustrated in FIG. 1. The coupling of the centrifuge chamber with the drive member of the centrifuge machine corresponds to that of a screw head, preferably a screw head of the type intended to mesh with an electrical screwdriver, a large variety of which exist. Other drive systems are also conceivable. The opposite end of the centrifuge chamber 1 has a tubular opening 1b, concentric with the axis of rotation of the chamber, in order to receive a member 5 causing this chamber 1 to interact with the outside. A rotary joint is provided at the tubular opening 1b. This joint may be material or dynamic and serves to isolate the centrifuge chamber from any outside contamination. A dynamic joint is understood to be any device without a material joint capable of forming a sterile barrier opposing the entry of air into the centrifuge chamber, for example by creating a slight excess pressure in the chamber, thus causing leakage of gas exiting this chamber, therefore preventing the entry of outside air.

The member 5 causing the centrifuge chamber 1 to interact with the outside comprises an internal part for supplying the chamber 1 with blood to be centrifuged and for draining the separate components thereof. Given that the mode of separation used by the centrifuge chamber 1 does not form part of the invention and is not necessary for its understanding, it suffices to specify that the interaction member 5 comprises a central tube 5a for bringing blood into the chamber and at least two peripheral tubes 5b, 5c for draining the separated components, in particular the plasma and the erythrocytes.

Figure 4:
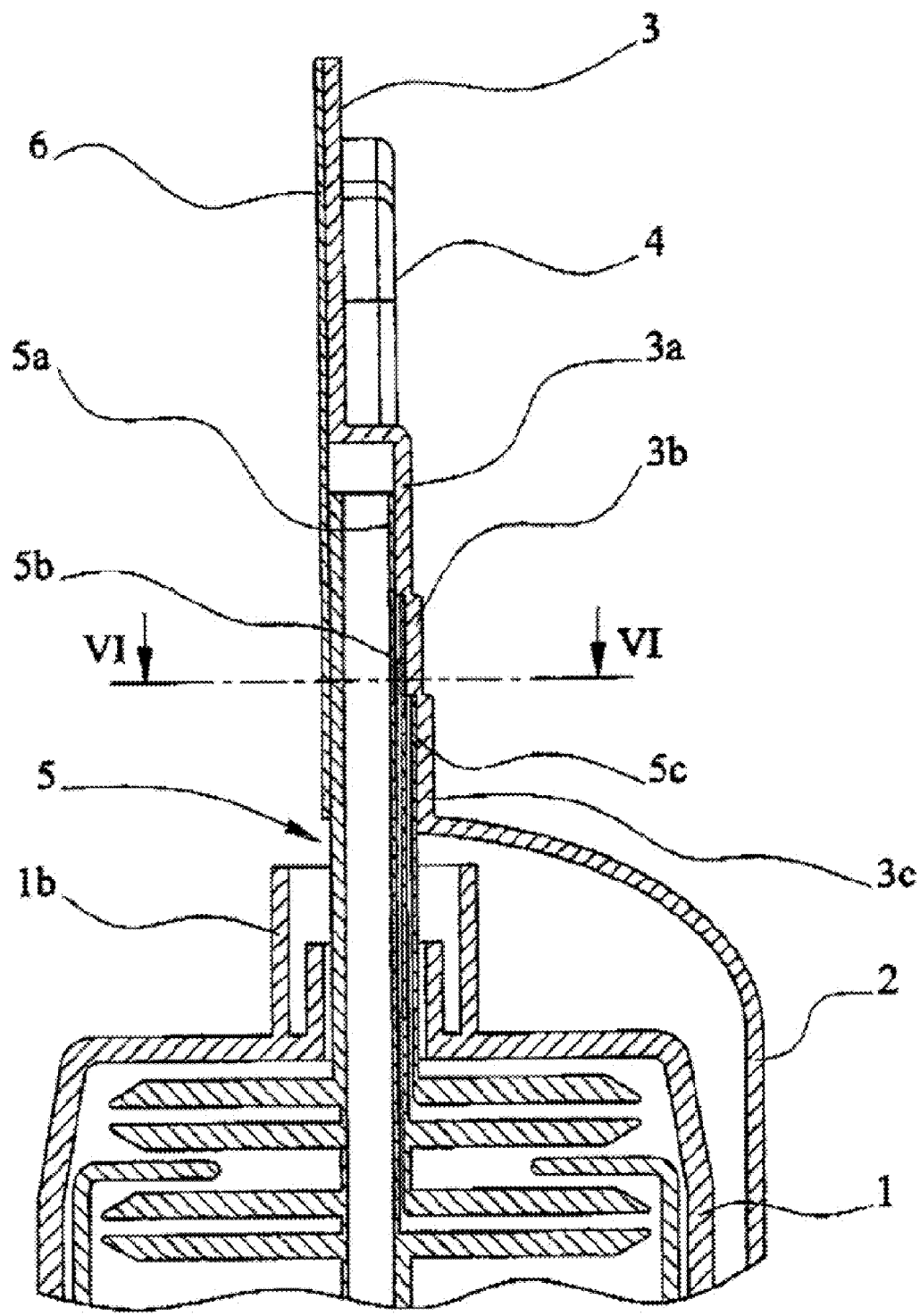
FIG. 4 is a sectional view along IV-IV of FIG. 2.
Figure 5:
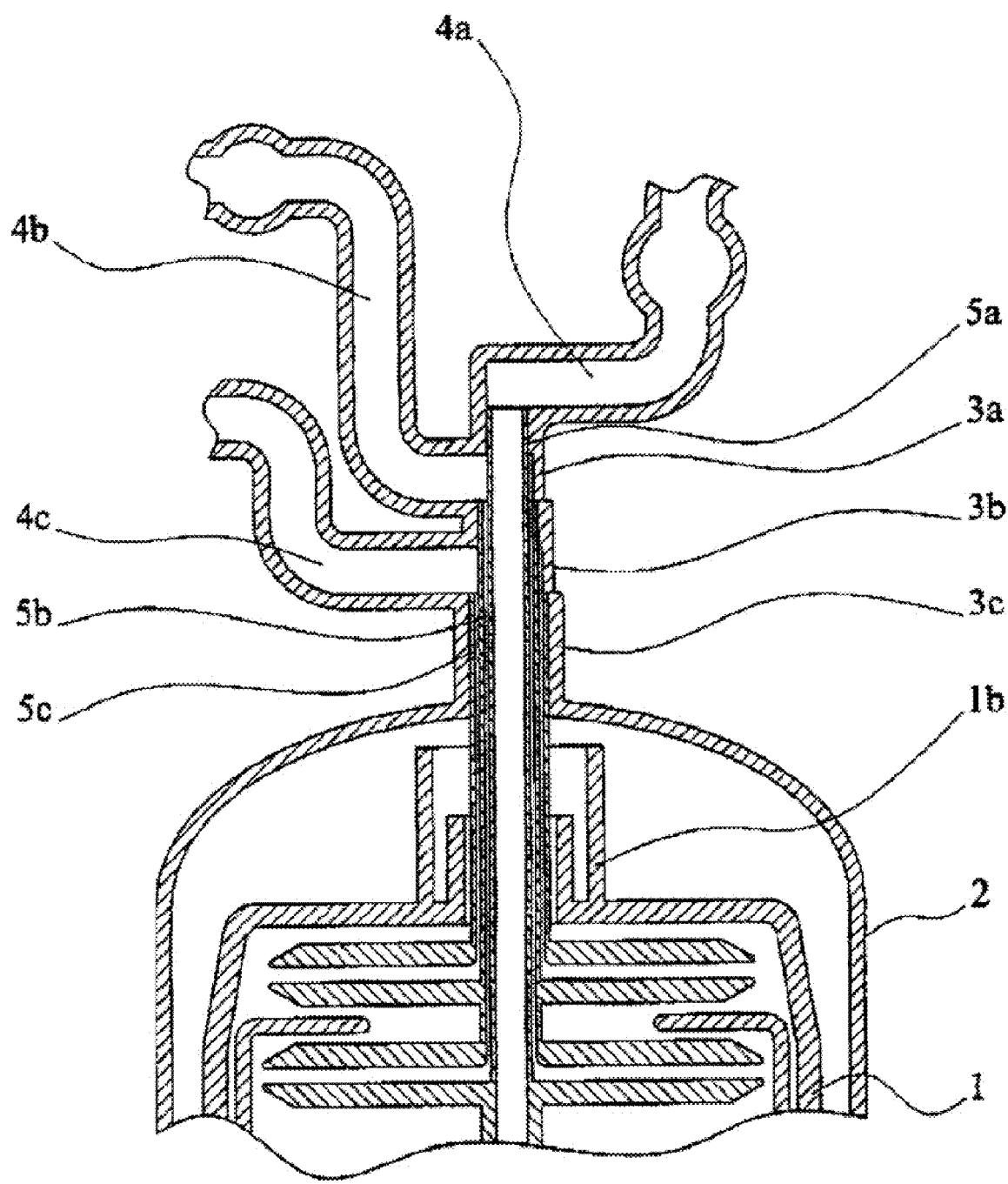
FIG. 5 is a sectional view along V-V of FIG. 6.
Figure 6:
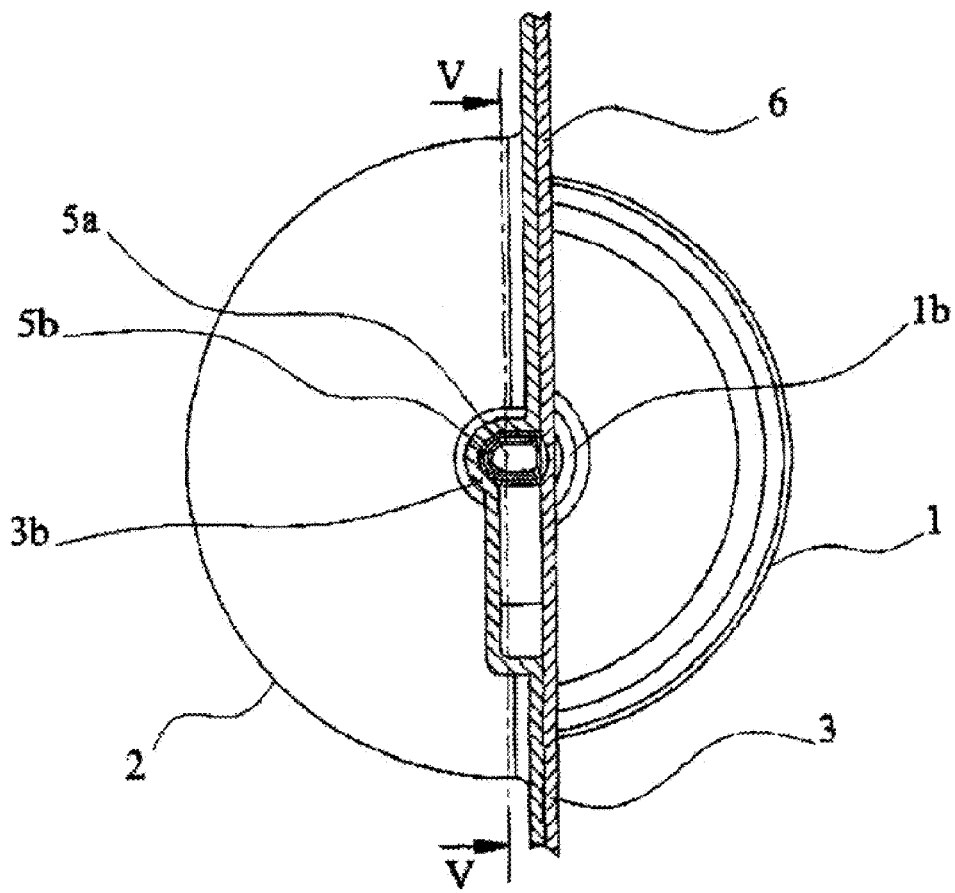
FIG. 6 is a sectional view along VI-VI of FIG. 4.

As can be seen in FIGS. 4 and 5, the outer ends of the tubes 5a, 5b, 5c are stepped and are housed in three respective seats 3a, 3b, 3c of complementary shapes, formed in the planar support 3 and against which the respective adjacent surfaces of the tubes 5a, 5b, 5c and of the seats 3a, 3b, 3c are fixed to each other, preferably by ultrasonic welding. Each of the seats 3a, 3b, 3c causes the tubes 5a, 5b, 5c to interact with one of the channels 4a, 4b, 4c of the network of channels 4 formed in the planar support 3.

Due to the fact that both the case 2 and the planar support 3, which advantageously form a single piece obtained by injection, and the member 5 causing the centrifuge chamber to interact are made of a hard plastic, when this centrifugation assembly is assembled after fixing the outside ends of the tubes 5a, 5b, 5c of the member 5 into the respective seats 3a, 3b, 3c of the planar support 3, this centrifugation assembly forms a non-deformable whole that can therefore be mounted very easily with one hand onto the centrifuge machine M. The open ends of the tubes, formed by the channels 4a, 4b, 4c laterally closed by the membrane 6 are connected beforehand to flexible pouches P1, P2, P3, respectively containing the blood and at least the plasma and the erythrocytes, and therefore not requiring any mounting.

Figure 7:
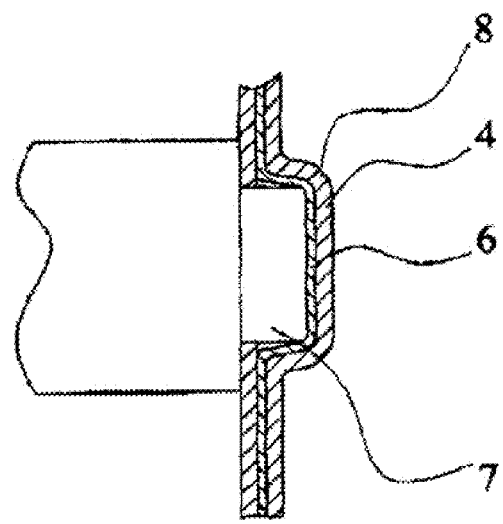
FIG. 7 is a detailed sectional view along VII-VII of FIG. 1.

The flexible membrane 6 serves to laterally close the channels 4a, 4b, 4c and at the same time, as illustrated by FIG. 7, it allows the plungers 7 of the centrifuge machine to deform this membrane 6 at determined locations. These plungers 7 enable the opening and closing of the channels 4a, 4b, 4c to be controlled, thus serving as clamps for controlling the flow into the various tubes by deforming the membrane 6 into a cavity 8 formed along the channels 4a, 4b, 4c. Another plunger also makes it possible to control pumping operations for circulating the fluid in the channels 4a, 4b, 4c by deforming the membrane 6 into a larger cavity 9, such as that illustrated in FIG. 1. To this end, this pumping plunger is moved in synchronization with the plungers 7 serving as clamps.

Figure 8:
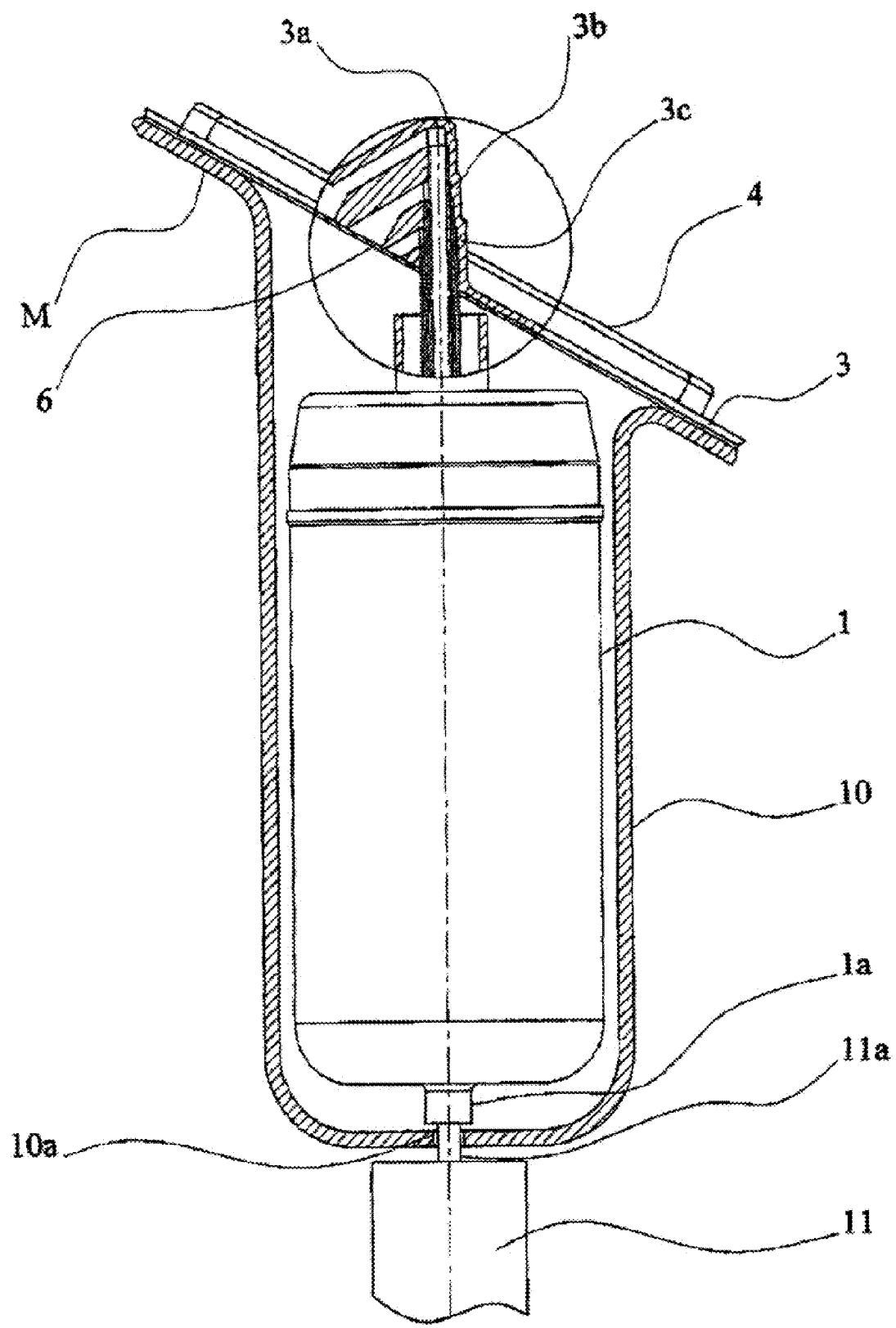
FIG. 8 is a side elevation view, partly sectional, of a second embodiment of the invention.

The second embodiment illustrated by FIG. 8 essentially differs from the preceding embodiment in that the case 2 is eliminated. The planar support 3 in which the network of channels 4 is formed by injection of a rigid plastic into a mold. In this embodiment, as in the preceding embodiment, the three seats 3a, 3b, 3c are again found, into which the respective tubes 5a, 5b, 5c for causing them to interact with the respective channels of the network of channels 4 formed in the support 3 are fixed, preferably by ultrasonic welding. Instead of the plane of the planar support 3 being parallel with the axis of rotation of the centrifuge chamber 1, it is inclined relative to this axis of rotation. The angle of inclination is given by the inclination of the upper surface of the centrifuge machine. It is also possible to imagine that this upper surface is horizontal and that the support 3 is then perpendicular to the axis of rotation of the centrifugation rotor.

In this variant, the case 2 which was joined to the support 3 is replaced by a housing 10 of the centrifuge machine M, the base of which has an opening 10a for allowing through a drive shaft 11a of a drive motor 11, the end of which meshes with the coupling element 1a of the centrifuge chamber 1. As in the preceding embodiment, the channels 4 are laterally closed by a flexible membrane 6. It is also possible to imagine replacing the case 2 of the first embodiment with one wall of the machine M.

This variant without the case 2 of the preceding embodiment makes it possible to reduce the price of the disposable part. The housing 10 of the centrifuge machine M in which the centrifuge chamber 1 is housed also makes it possible to provide better safety than the case 2 of the disposable assembly of the preceding embodiment.

Figure 9:
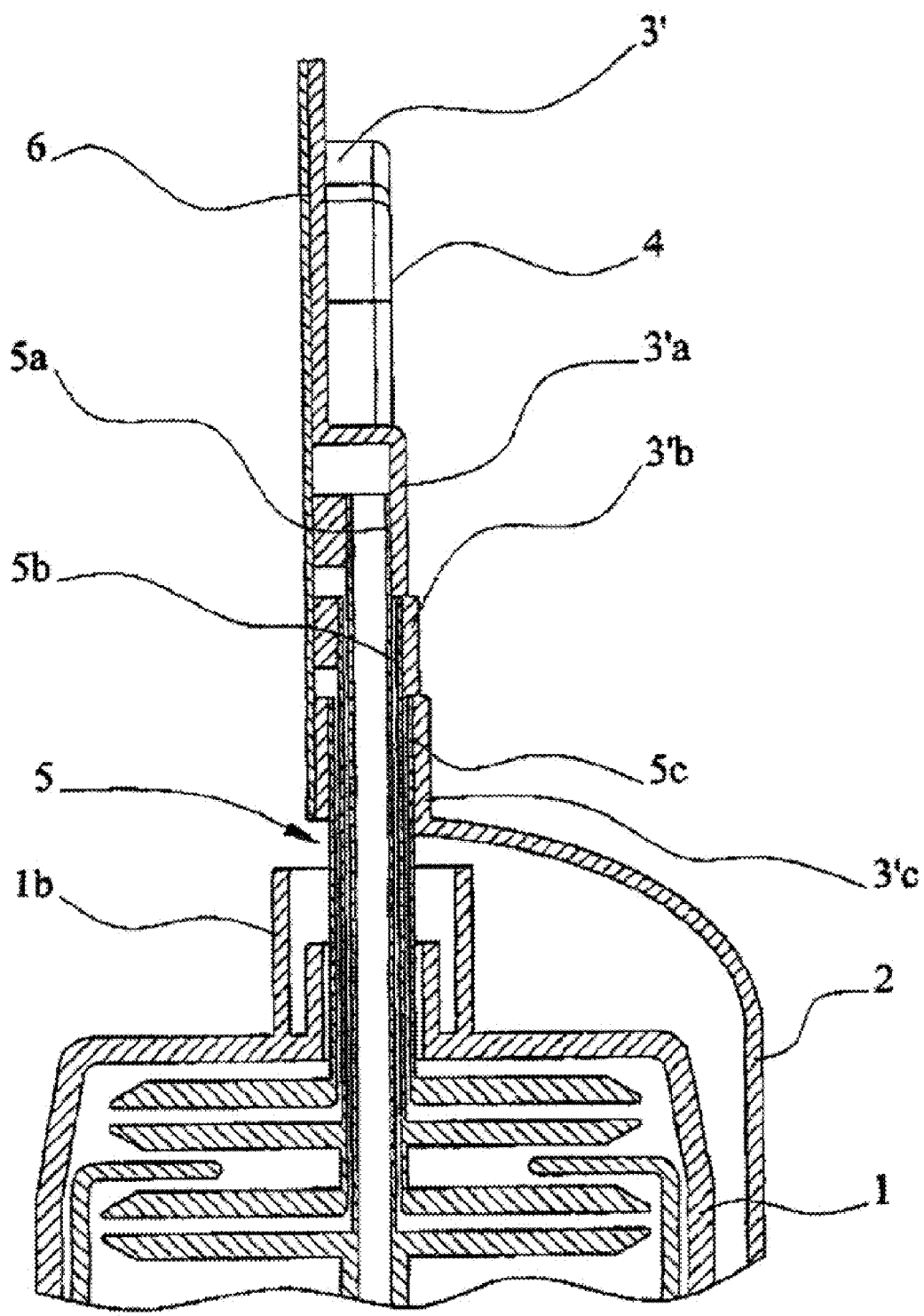
FIG. 9 is a variant of FIG. 4.
Figure 10:
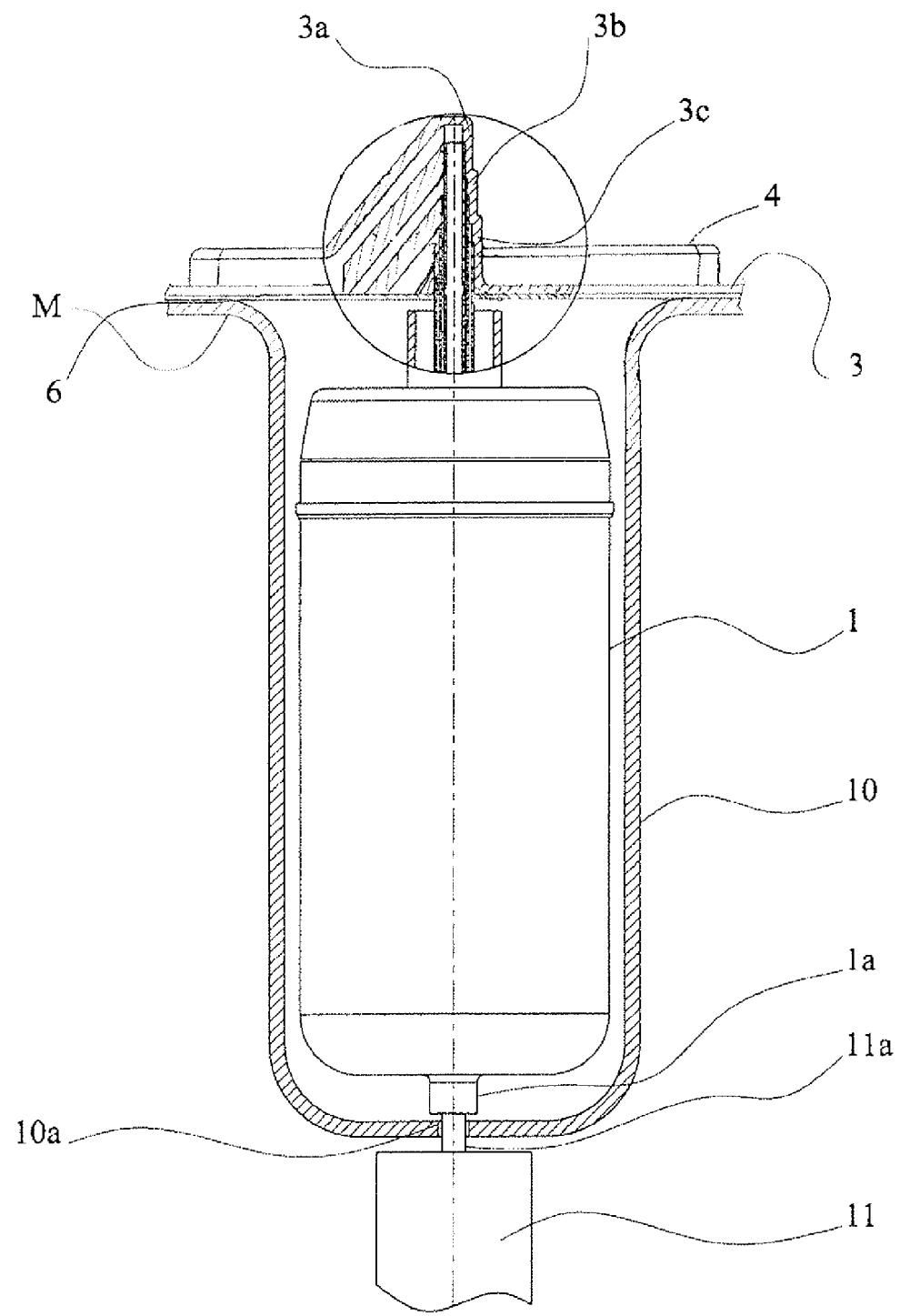
FIG. 10 is an illustrative view of a variant showing a planar support perpendicular to the axis of rotation.

FIG. 9 illustrates a variant in which the seats 3'a, 3'b and 3'c of the support 3' for fixing the tubes 5a, 5b, 5c are no longer semicylindrical, as in the example of FIG. 4, but are formed by cylindrical parts that hence completely surround the ends of the tubes 5a, 5b, 5c enabling better fixing.

By contrast, while the support 3 and the case 2 of FIG. 4 may be produced by hot working a thermoplastic sheet in the cavity of a mold, the variant of FIG. 9 can only be obtained by an injection technique and is therefore more expensive.

The previously described examples relate to the use of the disposable assembly for the separation of blood, in particular the continuous separation of blood. The same assembly could equally well be used for the washing of blood products by centrifugation.

It may, for example, be the deglycerolization of packed red blood cells before their injection into a patient, glycerol being a compound added to the packed red blood cells to improve their conservation, without hemolysis, at low temperature.

It may also be the washing of blood intended for autologous transfusion. In this case the patient's blood is collected via drainage tubes or via a suction cannula. Having been roughly filtered, the red blood cells are concentrated by centrifugation, then washed by injecting saline solution into the centrifuge chamber to remove the impurities and to separate them from the denser packed red blood cells. The washed red blood cells are finally extracted and collected in a collection pouch before their reinjection into the patient.

It is also possible to imagine washing the blood in batches. To this end, the blood to be treated is injected into the centrifuge chamber via the central tube 5a. In this case, the disposable assembly therefore comprises only a single outlet tube 5b through which the least dense fraction of the fluid is extracted. Next, the centrifuge chamber 1 is stopped to allow the more dense residual fraction to fall to the base of this chamber. This residual fraction is then extracted by siphoning through the supply tube 5a.

Current blood separation or autologous transfusion systems use pumps to control the flow rates entering and leaving the centrifuge chamber. They may be peristaltic pumps, requiring the presence of flexible tubes on the single-use assembly, or diaphragm pumps in the case of a semi-rigid assembly, such as described in the preceding examples.

Figure 1:
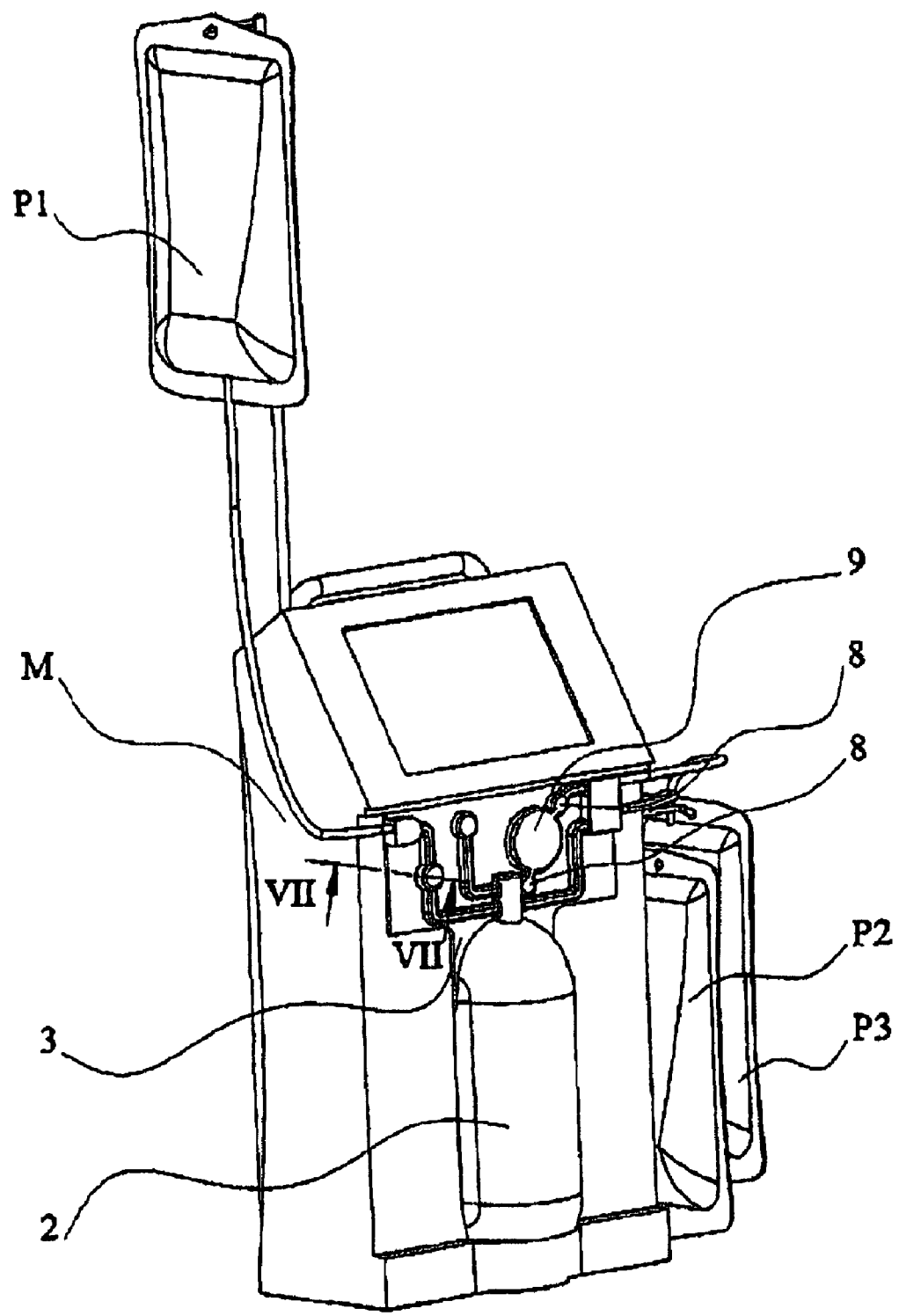
FIG. 1 is a perspective view of a centrifuge machine on which the disposable assembly is mounted.

It is, however, also possible to cause the fluid to circulate toward the centrifuge chamber 1 by raising the height of the supply pouch P1 relative to the centrifuge chamber so as to create a motor liquid column, as shown in FIG. 1, and by adjusting the value of the flow rate by means of adjustable throttling using a plunger 7, as shown by FIG. 7.

Similarly, the pressure necessary to transfer components leaving the centrifuge chamber through to the collection pouches P2, P3 may be obtained by converting the rotational kinetic energy of the fluids inside the centrifuge chamber into potential energy of pressure during their extraction. The adjustment of the flow rate is then also obtained by means of adjustable throttling.

The use of pumps is therefore not indispensable.

The invention claimed is:

1. A disposable assembly for separating blood or the washing of a blood component by centrifugation, comprising a circular centrifuge chamber made of a rigid plastic, comprising, at an end lying on its axis of rotation, an element shaped in order to mesh with a drive member of a centrifuge machine and, at an opposite end, a member for interaction of said chamber with the outside made of a rigid plastic, connected to said centrifuge chamber by a rotary joint and passed through by a tube to supply this chamber and by at least one outlet tube for draining at least one of the separate constituents, a support made of a rigid plastic in which a network of channels is formed in order to connect said tubes respectively to a supply reservoir for the blood to be separated and to at least one reception reservoir for a separated constituent, elements for laterally closing this network of channels in a sealed manner and means for circulating the fluids through this network of channels from the supply reservoir to the reception reservoirs wherein the ends of said tubes passing through said member causing said chamber to interact with the outside, concentric with said axis of rotation, are adjacent to the respective ends of said channels, in that the ends of said tubes have surfaces complementary to the surfaces of the ends of said respective channels, and in that these complementary surfaces are fixed to each other by joints in a sealed manner so that said support and said member for causing said chamber to interact with the outside form a rigid assembly.

2. The assembly as claimed in claim 1, in which the fixings between the surfaces of the respective ends of said tubes and said channels are non-removable fixings.

3. The assembly as claimed in claim 2, in which said support is formed in a single piece with a case.

4. The assembly as claimed in claim 3, having an opening for at least partly receiving the centrifuge chamber, the part of this case opposite that which is adjacent to said support having a second opening to allow the passage of said element shaped to mesh with drive means of the centrifuge machine.

5. The assembly as claimed in claim 4, in which said support is a planar support.

6. The assembly as claimed in claim 3, in which said support is a planar support.

7. The assembly as claimed in claim 2, in which said support is a planar support.

8. The assembly as claimed in claim 7, in which said planar support is inclined relative to the axis of rotation of said centrifuge chamber.

9. The assembly as claimed in claim 7, in which said planar support is perpendicular to the axis of rotation of said centrifuge chamber.

10. The assembly as claimed in claim 1, in which said support is formed in a single piece with a case.

11. The assembly as claimed in claim 10, having an opening for at least partly receiving the centrifuge chamber, the part of this case opposite that which is adjacent to said support having a second opening to allow the passage of said element shaped to mesh with drive means (11a) of the centrifuge machine.

12. The assembly as claimed in claim 11, in which said support is a planar support.

13. The assembly as claimed in claim 12, in which said planar support is inclined relative to the axis of rotation of said centrifuge chamber.

14. The assembly as claimed in claim 12, in which said planar support is perpendicular to the axis of rotation of said centrifuge chamber.

15. The assembly as claimed in claim 10, in which said support is a planar support.

16. The assembly as claimed in claim 15, in which said planar support is inclined relative to the axis of rotation of said centrifuge chamber.

17. The assembly as claimed in claim 15, in which said planar support is perpendicular to the axis of rotation of said centrifuge chamber.

18. The assembly as claimed in claim 1, in which said support is a planar support.

19. The assembly as claimed in claim 18, in which said planar support is inclined relative to the axis of rotation of said centrifuge chamber.

20. The assembly as claimed in claim 18, in which said planar support is perpendicular to the axis of rotation of said centrifuge chamber.

* * * * *